(12) United States Patent
De La Sotta (10) Patent No.: US 10,117,391 B2
(45) Date of Patent: Nov. 6, 2018

(54) APPARATUS AND METHOD FOR DELIVERING POLLEN FOR DIRECTED POLLINATION OF PLANTS

(71) Applicant: PIONEER HI-BRED INTERNATIONAL, INC., Johnston, IA (US)

(72) Inventor: Jose Manuel De La Sotta, Kailu, HI (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 482 days.

(21) Appl. No.: 14/776,208

(22) PCT Filed: Mar. 6, 2014

(86) PCT No.: PCT/US2014/021269
§ 371 (c)(1),
(2) Date: Sep. 14, 2015

(87) PCT Pub. No.: WO2014/149866
PCT Pub. Date: Sep. 25, 2014

(65) Prior Publication Data
US 2016/0037740 A1    Feb. 11, 2016

Related U.S. Application Data

(60) Provisional application No. 61/784,503, filed on Mar. 14, 2013.

(51) Int. Cl.
*A01H 1/02* (2006.01)
*A01G 22/00* (2018.01)

(52) U.S. Cl.
CPC .............. *A01H 1/025* (2013.01); *A01G 22/00* (2018.02); *A01H 1/02* (2013.01)

(58) Field of Classification Search
CPC ..... A01H 1/025; A47G 21/186; A47G 21/189
See application file for complete search history.

(56) References Cited

U.S. PATENT DOCUMENTS 3,189,171 A  *  6/1965  Miller .................. A47G 21/189
                                                      206/229
4,087,937 A       5/1978  Meador
(Continued)

FOREIGN PATENT DOCUMENTS

FR          2866784 A1       9/2005
WO     WO-8607529 A1  * 12/1986  ........... A47G 21/189
(Continued)

OTHER PUBLICATIONS

International Search Report—PCT/US2014/021269—dated Jun. 4, 2014.

*Primary Examiner* — Kristen C Hayes (57) ABSTRACT

Apparatuses and methods for delivering pollen for the directed pollination of plants are provided herein. One example embodiment comprises a rigid tube having a first end, a second end, and a channel defined therebetween, wherein the rigid tube is configured to receive the tassel of the maize plant proximate the first end and to interact with the ear shoot of the maize plant proximate the second end, and wherein the channel defines a path between the tassel and the ear shoot so as to enable transfer of pollen from the tassel to the ear shoot. In another example embodiment, the rigid tube may be telescoping such that the overall length of the rigid tube may be adjustable. In another example embodiment, the apparatus may include a fan configured to propel air onto the tassel to aid in the transfer of pollen through the channel to the ear shoot. The apparatuses and methods are applicable for directed cross-pollination between different plants of the same species and plants of different species.

10 Claims, 9 Drawing Sheets

(56) References Cited

U.S. PATENT DOCUMENTS 4,159,596 A * 7/1979 Downing ............... A01H 1/025
  47/1.41
2013/0068854 A1* 3/2013 Miracle .................. A47G 21/18
  239/33

FOREIGN PATENT DOCUMENTS

| WO | WO-9112755 A1 * | 9/1991 | ............. A47G 21/18 |
| WO | 2012/125593 A2 | 9/2012 | |

* cited by examiner

APPARATUS AND METHOD FOR DELIVERING POLLEN FOR DIRECTED POLLINATION OF PLANTS

FIELD OF THE INVENTION

Various embodiments of the present invention relate generally to an apparatus and method for delivering pollen. More specifically, embodiments of the present invention provide an apparatus and method for delivering pollen to facilitate directed pollination.

BACKGROUND OF THE INVENTION

For a variety of reasons, plant species may be intentionally bred. For example, in some applications plant species are intentionally bred to form hybrid plant species. In some applications, hybrid plants are bred to exhibit various desirable traits. Such traits may include, for example, improved yield characteristics, and improved agronomic quality, resistance to heat and drought, and resistance to disease and insect damage. In general, plants may be capable of self-pollination, cross-pollination, or both. Self-pollination describes pollination using pollen from one flower that is transferred to the same or another flower of the same plant. Cross-pollination describes pollination using pollen delivered from a flower of a different plant from a different family, line, or species.

Plants that have been self-pollinated and selected for many generations become homozygous at almost all gene loci and produce a uniform population of true breeding progeny. This could also include Doubled Haploid lines, completely homozygous individuals, produced within a single generation. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

Maize (*Zea mays* L.), often referred to as corn in the United States, can be bred by both self-pollination and cross-pollination techniques. Maize has separate male and female flowers on the same plant. The male flowers are located on the tassel and the female flowers are located on the ear. Natural pollination occurs in maize when grains of pollen from the tassel land on the silks that protrude from the tops of the ears.

The development of a hybrid maize variety in a maize seed production program may involve three steps: (1) the selection of plants from various germplasm pools for initial breeding crosses; (2) self-pollination of the selected plants from the breeding crosses for several generations to produce a series of inbred lines, which, individually breed true and are highly uniform or selected plants from completely homozygous doubled haploids generated from the breeding crosses; and (3) crossing a selected inbred line with selected inbred line to produce the hybrid progeny.

An important consequence of the homozygosity and homogeneity of the inbred lines is that the hybrid between a defined pair of inbreds may be reproduced indefinitely as long as the homogeneity of the inbred parents is maintained. Once the inbreds that create a superior hybrid have been identified, a continual supply of the hybrid seed can be produced using these inbred parents and the hybrid corn plants can then be generated from this hybrid seed supply. Accordingly, development and production of maize seed may require controlled pollination at one or more steps, as described above.

BRIEF SUMMARY

In various embodiments the present invention provides apparatuses and methods for directed pollination of plants. In one embodiment an apparatus is provided for directed pollination of a maize plant, wherein the maize plant defines a tassel and an ear shoot. The apparatus comprises a rigid tube having a first end, a second end, and a channel defined therebetween, wherein the rigid tube is configured to receive the tassel of the maize plant proximate the first end, wherein the rigid tube is configured to interact with the ear shoot of the maize plant proximate the second end, and wherein the channel defines a path between the tassel and the ear shoot so as to enable transfer of pollen from the tassel to the ear shoot.

In another embodiment, the rigid tube is a telescoping rigid tube such that the overall length of the rigid tube is adjustable. In another embodiment, the second end defines a second end opening that is configured to receive the ear shoot of the maize plant. In another embodiment, the second end is configured to interact with a shoot bag such that pollen may transfer from the tassel to the ear shoot of the maize plant through the channel and shoot bag. In another embodiment, the first end is configured to interact with a tassel bag such that the tassel is received into the tassel bag. In another embodiment, the rigid tube defines an opening proximate the first end, and the opening is configured to receive the tassel therethrough. In another embodiment, the rigid tube is made from at least one of the following materials: PVC plastic, polycarbonate, polypropylene, plastic, cardboard, or a compostable material. In another embodiment, the path is enclosed so as to prevent unintended cross-pollination. In another embodiment, the channel is defined by a smooth surface to prevent obstruction of pollen transferring from the tassel to the ear shoot. Another embodiment further comprises a fan attached to the rigid tube such that the fan is fluidly connected to the channel, wherein the fan is configured to create air flow to transfer the pollen through the channel to the ear shoot.

In another embodiment a method if provided for directed pollination of a maize plant, wherein the maize plant comprises a tassel and an ear shoot. The method comprises providing a rigid tube having a first end, a second end, and a channel defined therebetween, and attaching the rigid tube to the maize plant such that the tassel is received proximate the first end and the ear shoot is positioned to interact with the channel proximate the second end such that the channel defines a path between the tassel and the ear shoot so as to enable transfer of pollen from the tassel to the ear shoot.

Another embodiment further comprises attaching a fan to the rigid tube such that the fan is fluidly connected to the channel, wherein the fan is configured to create air flow to transfer the pollen through the channel to the ear shoot. In another embodiment, the rigid tube is a telescoping rigid tube such that the overall length of the rigid tube is adjustable. In another embodiment, attaching the rigid tube comprises positioning the ear shoot within a second end opening of the rigid tube proximate the second end. Another embodiment further comprises attaching a shoot bag to the rigid tube proximate the second end such that the shoot bag interacts with the ear shoot and pollen transfers from the tassel to the ear shoot of the maize plant through the channel and the shoot bag. Another embodiment further comprises attaching a tassel bag to the rigid tube proximate the first end and receiving the tassel in the tassel bag. In another embodiment, attaching the rigid tube comprises inserting the tassel into an opening proximate the first end of the rigid tube. In another embodiment, the channel is rigid so as to define a smooth surface to prevent obstruction of pollen transferring from the tassel to the ear shoot. In another embodiment, attaching the rigid tube to the maize plant occurs at any time before flower emergence to later in flower development.

In another embodiment, an apparatus is provided for directed cross-pollination of a maize plant. The apparatus comprises a rigid tube having a first end, a second end, and a channel defined therebetween, wherein the rigid tube is configured to receive a tassel of a first maize plant proximate the first end, wherein the rigid tube is configured to interact with the ear shoot of a second maize plant proximate the second end, and wherein the channel defines a path between the tassel of the first maize plant and the ear shoot of the second maize plant so as to enable transfer of pollen from the tassel to the ear shoot.

In another embodiment, a method for directed cross-pollination of a maize plant is provided. The method comprises providing a rigid tube having a first end, a second end, and a channel defined therebetween, attaching the rigid tube to a first maize plant such that a tassel of the first maize plant is received proximate the first end; attaching the rigid tube to a second maize plant such that an ear shoot of the second maize plant is positioned to interact with the channel proximate the second end such that the channel defines a path between the tassel and the ear shoot so as to enable transfer of pollen from the tassel to the ear shoot.

In another embodiment, an apparatus for directed cross-pollination of a plant is provided. The apparatus comprises a rigid tube having a first end, a second end, and a channel defined therebetween, wherein the rigid tube is configured to receive a pollen source portion of a plant of a first species proximate the first end, wherein the rigid tube is configured to interact with a pollen receiving portion of a plant of a second species proximate the second end, and wherein the channel defines a path between the pollen source portion of the plant of the first species and the pollen receiving portion of the plant of the second species so as to enable transfer of pollen from the pollen source portion to the pollen receiving portion.

In another embodiment, a method for directed cross-pollination of a plant is provided. The method comprises providing a rigid tube having a first end, a second end, and a channel defined therebetween, attaching the rigid tube to a pollen source portion of a plant of a first species such that the pollen source portion of the plant of the first species is received proximate the first end; and attaching the rigid tube to a pollen receiving portion of a plant of a second species such that the pollen receiving portion of the plant of the second species is positioned to interact with the channel proximate the second end such that the channel defines a path between the pollen source portion and the pollen receiving portion so as to enable transfer of pollen from the pollen source portion to the pollen receiving portion.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Directed pollination of plants, for example during self-pollination or cross-pollination, may involve manually collecting and delivering pollen. Manually collecting and delivering pollen is often tedious, time consuming, and very labor intensive. For example, a worker may manually collect pollen by knocking it from the tassel into a bag. Further, the worker may then manually sprinkle the pollen onto the silks of the maize plant which have been covered with a bag so as to prevent pollination with pollen other than the collected grains of pollen. Thus, collection of pollen and directed pollination using the collected pollen may involve many manual steps that may be conducted over the course of one or more days.

Figure 1:
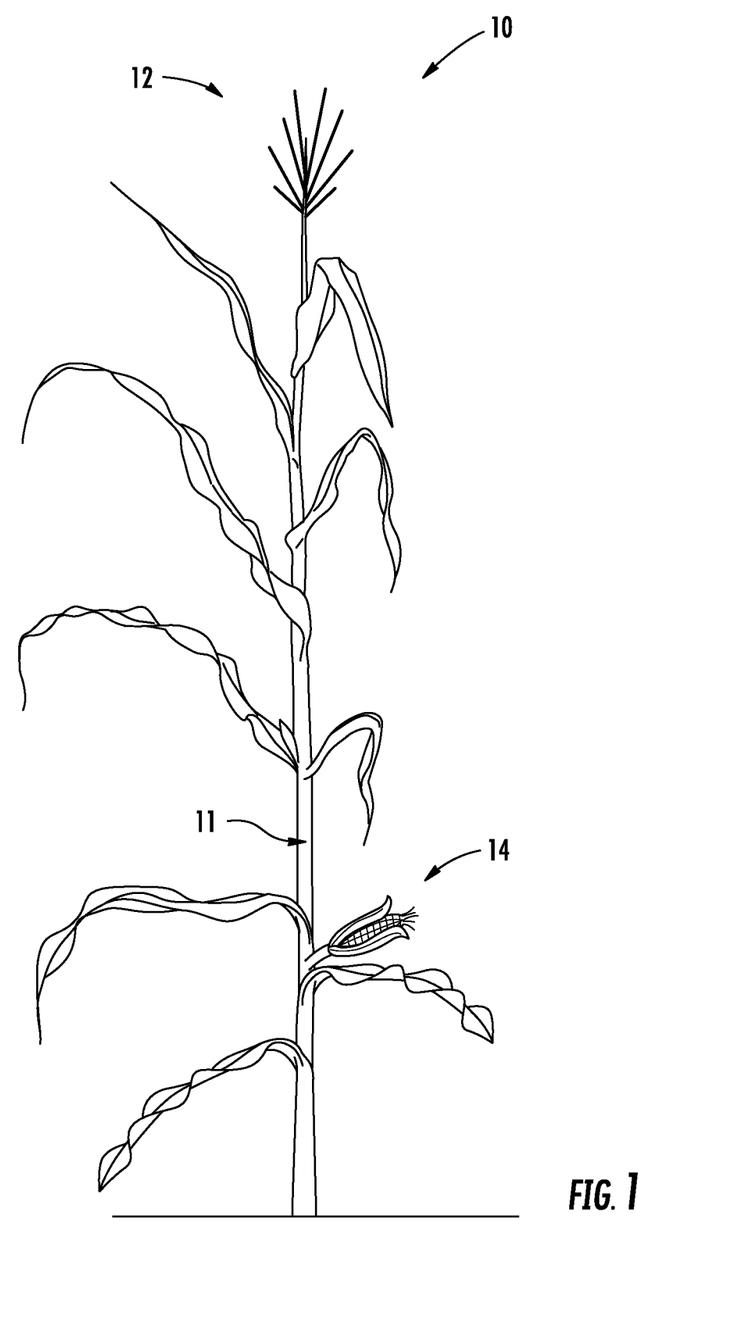
FIG. 1 illustrates a maize plant having a tassel, a stalk, and an ear shoot.

Accordingly, embodiments of the present invention provide an apparatus and method for delivering pollen for directed pollination of plants. In this regard, FIG. 1 illustrates a maize plant 10 having a tassel 12, stalk 11, and an ear shoot 14. It should be noted that while maize plants are shown in FIG. 1 and referred to throughout this specification, embodiments of the present invention are also useful for pollination of other types of plants.

Figure 2:
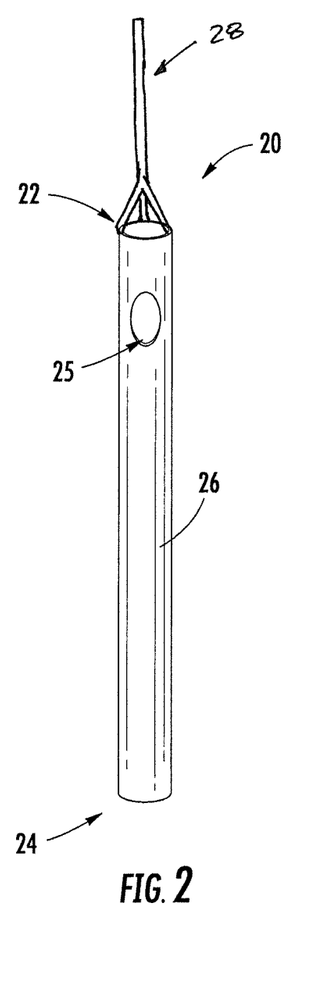
FIG. 2 illustrates a directed pollination apparatus configured for delivering grains of pollen in accordance with an example embodiment of the present invention.

FIG. 2 illustrates an embodiment of a directed pollination apparatus 20 configured for delivering grains of pollen in accordance with an example embodiment of the present invention. In the depicted embodiment, the directed pollination apparatus 20 may comprise a hollow rigid tube 26 having a first end 22 (which may define a first end opening) and a second end 24 (which may define a second end opening) and a channel defined therebetween. In the depicted embodiment, the directed pollination apparatus 20 is constructed of PVC plastic, however in various other embodiments, the directed pollination apparatus may be made of a variety of materials, including, but not limited to, metal materials, other plastic materials including polycarbonate, polypropylene, cardboard materials, fully compostable materials, and/or any combination of these or other suitable materials. In the various embodiments the rigid tube 26 includes an opening 25 proximate the first end 22. The opening 25 is configured to receive the tassel of a maize plant and, in some embodiments, part of the top portion of the maize plant. In the depicted embodiment, the opening 25 has an elliptical shape, however in other embodiments the opening may have any other shape configured to receive the tassel of a maize plant. In some embodiments, a tassel bag support feature 28 may be included proximate the first end 22 of the directed pollination apparatus 20, and which may be configured to add structural strength to a tassel bag assembly.

Figure 3:
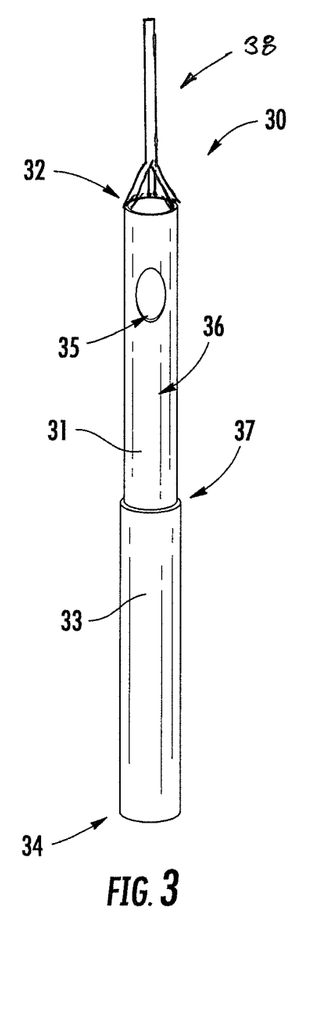
FIG. 3 illustrates a telescoping directed pollination apparatus for delivering grains of pollen in accordance with another example embodiment of the present invention.

FIG. 3 illustrates a directed pollination apparatus 30 configured for delivering grains of pollen in accordance with another example embodiment of the present invention. In the depicted embodiment, the directed pollination apparatus 30 comprises a telescoping hollow rigid tube 36. As will be explained in more detail below, a directed pollination apparatus with a telescoping rigid tube may be advantageous for use with plants where the distance between the male portion and the female portion varies across multiple plants. Although in various similar embodiments, a directed pollination apparatus having a telescoping rigid tube may have a variety of configurations, in the depicted embodiment the directed pollination apparatus 30 includes a rigid tube 26 having multiple sections (shown in the depicted embodiment as sections 31, 33), one or more of which slides into one or more others at a junction area (shown in the depicted embodiment as area 37). In such a manner, the overall length of the directed pollination apparatus may be adjustable. In the depicted embodiment, the upper section 31 overlaps the lower section 33 to avoid a gap at the interface that could make the apparatus vulnerable to contamination from foreign pollen. In some embodiments, a tassel bag support feature 38 may also be included proximate a first end 32 of the directed pollination apparatus 30.

Figure 4:
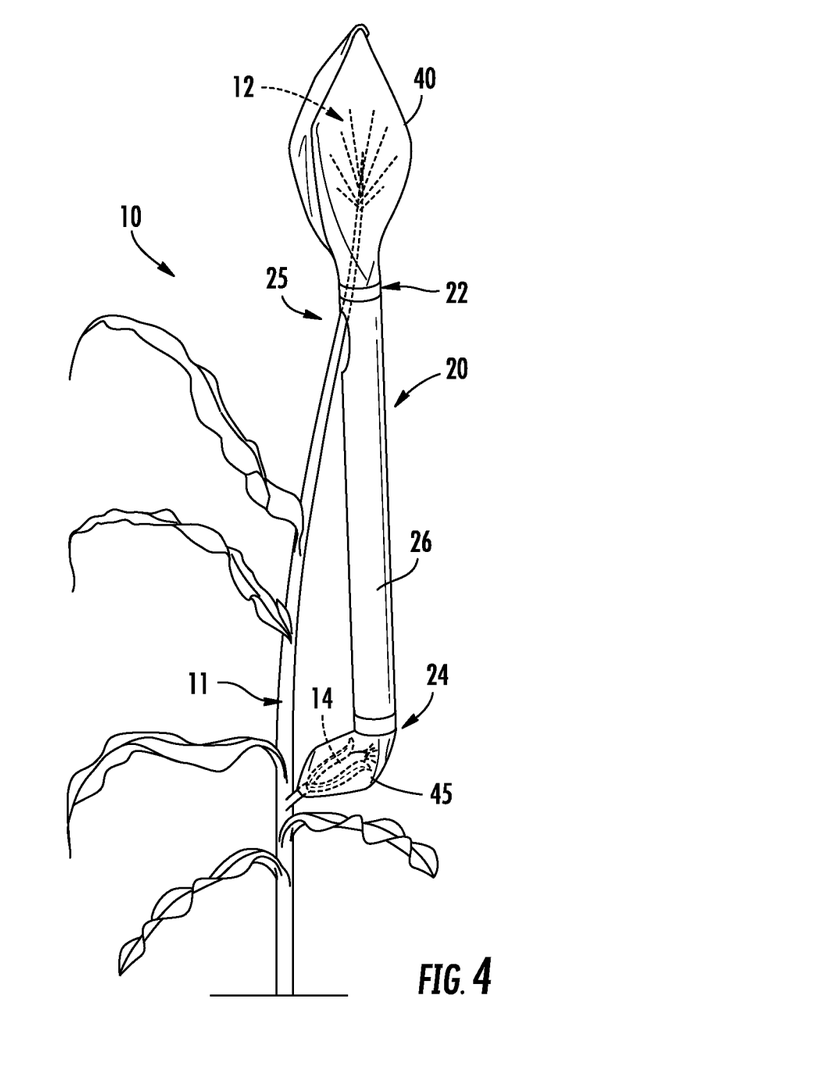
FIG. 4 illustrates a maize plant and a directed pollination apparatus configured for delivering grains of pollen in accordance with an example embodiment of the present invention.

FIG. 4 illustrates a directed pollination apparatus 20 attached to a maize plant 10 in accordance with an example embodiment of the present invention. In the depicted embodiment, the directed pollination apparatus 20 comprises a hollow rigid tube 26 having a first end 22 and a second end 24 and a channel defined therebetween. An opening 25 is disposed in the rigid tube 26 proximate the first end 22, which is configured to receive the tassel 12 of the maize plant 10. In the depicted embodiment, a tassel bag 40 is attached to the first end 22 of the rigid tube 26, and a shoot bag 45 is attached to the second end 24 of the rigid tube 26. As will be explained in more detail below, the tassel bag 40 of the depicted embodiment is configured to receive the tassel 12 of the maize plant 10, and the shoot bag 45 is configured to receive the ear shoot 14 of the maize plant 10. In various embodiments, the tassel bag 40 and the shoot bag 45 may be made of one or more of a variety of materials configured to contain pollen grains and prevent cross-contamination. In such a manner, the tassel bag 40 and shoot bag 45 may be attached to the rigid tube 26 so as to minimize or eliminate the escape of pollen grains. In various embodiments, this may include attaching the tassel bag 40 and shoot bag 45 to the rigid tube 26 using a sealing material, which may include, but need not be limited to, adhesives, tapes, and/or heat or ultrasonic welds. In the depicted embodiment, the tassel bag 40 and the shoot bag 45 are constructed of a flexible material, which may be advantageous for plants having tassels and ear shoots with varying sizes; however, in other embodiments one or both of the tassel bag 40 or shoot bag 45 may be constructed of a rigid material. Such materials may include, but need not be limited to, metal materials, plastic materials (such as, for example, PVC or polycarbonate materials), cardboard materials, fully compostable materials, and/or any combination of these or other suitable materials. It should be noted that in other embodiments, a tassel bag need not be included as the rigid pipe 26 itself, or a portion or extension thereof, may be configured to interact with the tassel 12. Likewise, in other embodiments a shoot bag need not be included as the rigid pipe 26 itself, or a portion or extension thereof, may be configured to interact with the ear shoot 14.

Figure 5:
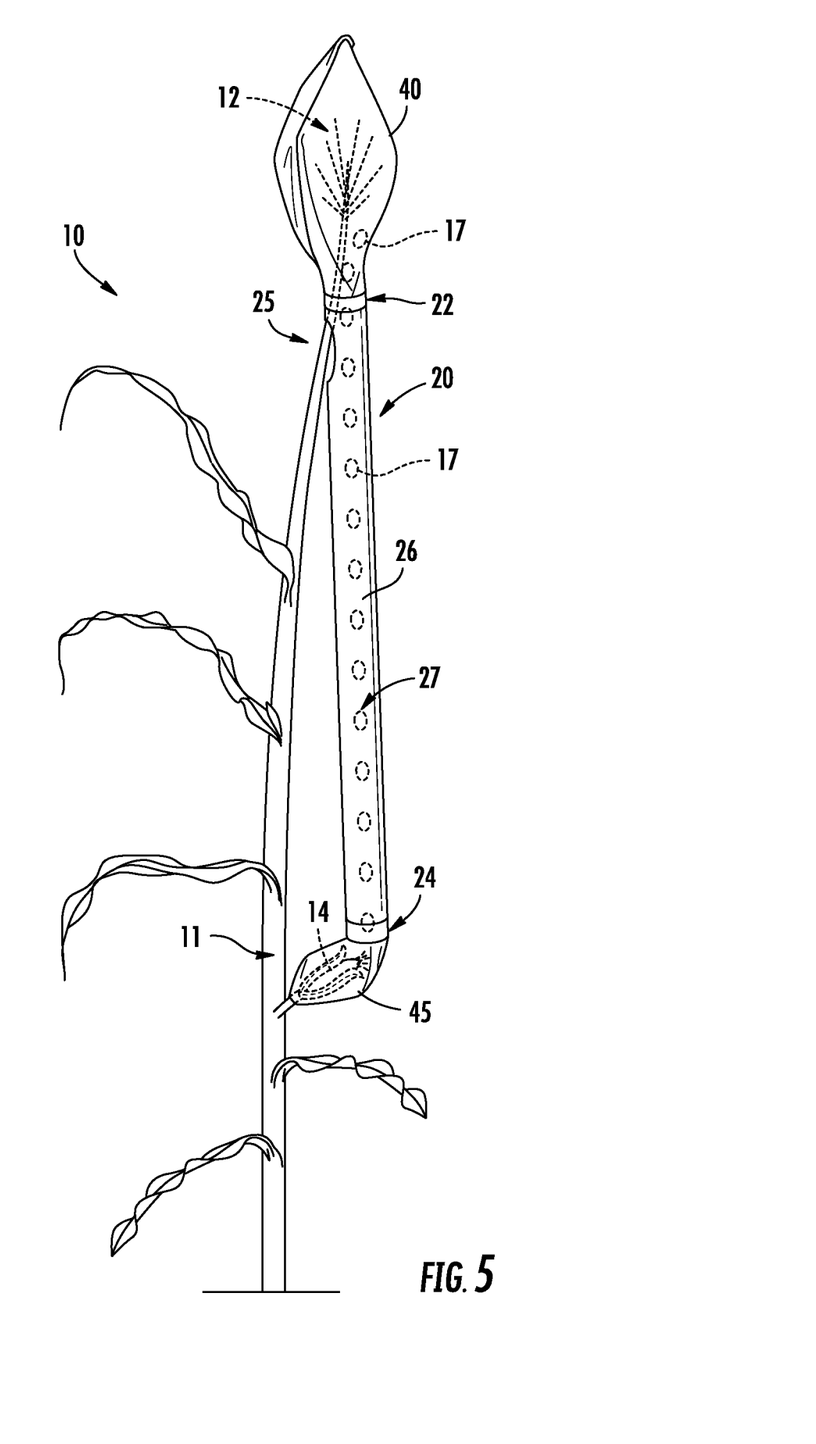
FIG. 5 illustrates a close-up view of a maize plant and a directed pollination apparatus configured for delivering grains of pollen in accordance with an example embodiment of the present invention.

FIG. 5 illustrates close-up view a directed pollination apparatus 20 attached to a maize plant 10 in accordance with an example embodiment of the present invention. The directed pollination apparatus 20 comprises a hollow rigid tube 26 having a first end 22, a second end 24, a channel defined therebetween, and an opening located proximate the first end 22. A tassel bag 40 is attached to the first end 22 and a shoot bag 45 is attached to the second end 24. In practice, the directed pollination apparatus 20 of the present invention is attached to a maize plant 10 prior to the release of pollen from the tassel 12 of the maize plant 10. In some embodiments, the rigid pipe 26 may be separately secured to the stalk 11 of the maize plant 10. In the depicted embodiment, the top portion of the maize plant 10 is inserted into the opening 25 of the rigid tube 36 and the shoot bag 45 is placed over the ear shoot 14. As such, the tassel 12 of the maize plant 10 is received by the rigid tube 26 and extends into the tassel bag 40, and the ear shoot extends into the shoot bag 45. In the depicted embodiment, the opening 25 is an elliptical opening, which allows the top portion of the maize plant 10 to be more easily received by the rigid tube 26 in the attached position. In such a manner, the top of the maize plant 10 may extend upward without excessive bending. This also allows the rigid tube 26 to be positioned so that it is in a relatively vertical position, thus providing an optimal path for the grains of pollen to reach the ear shoot 14.

As shown in FIG. 5, the shoot bag 45 may also be secured to a lower portion of the ear shoot 14 so as to contain any falling pollen grains inside the shoot bag 45. This may be accomplished in a variety of ways, including, but not limited to, securing the shoot bag 45 to the lower portion of the ear shoot using adhesives, tapes, wires, pipe cleaners, etc. In such a configuration, the rigid tube 26 of the apparatus 20 defines a path 27 for the pollen grains 17 (shown in the drawing, for simplicity, as a series of circles) to transfer from the tassel 12 to the ear shoot 14 once the tassel 12 of the maize plant 10 begins to shed pollen. In various embodiments the path 27 is enclosed so as to prevent cross-pollination. For example, in the depicted embodiment the tassel bag 40 is secured to the first end 22 of the rigid tube 26, and the shoot bag 45 is secured to the second end of the rigid tube 26 and the lower portion of the ear shoot 14.

In various embodiments, the channel defined by the rigid tube 26 may have a smooth surface in order to prevent obstruction of pollen grains transferring from the tassel 12 to the ear shoot 14. In some embodiments, a portion of the directed pollination apparatus 20 (such as, for example, one or more of the rigid tube 26, the tassel bag 40, or the shoot bag) may be electrically controlled (such as, for example, by grounding one or more of the components) so as to prevent the attraction of pollen grains to surfaces of the apparatus 20.

Figure 6A:
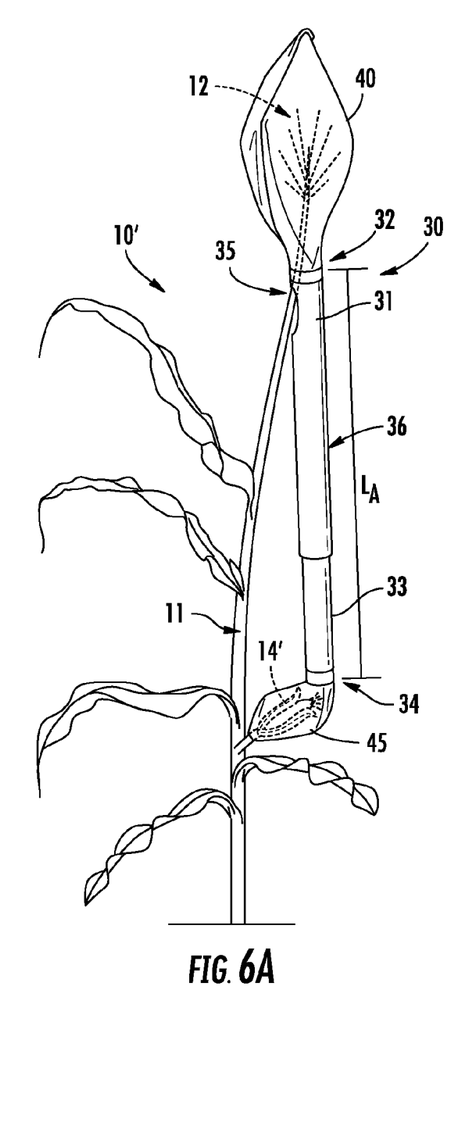
FIG. 6A illustrates a maize plant and a telescoping directed pollination apparatus configured for delivering grains of pollen in accordance with an example embodiment of the present invention.
Figure 6B:
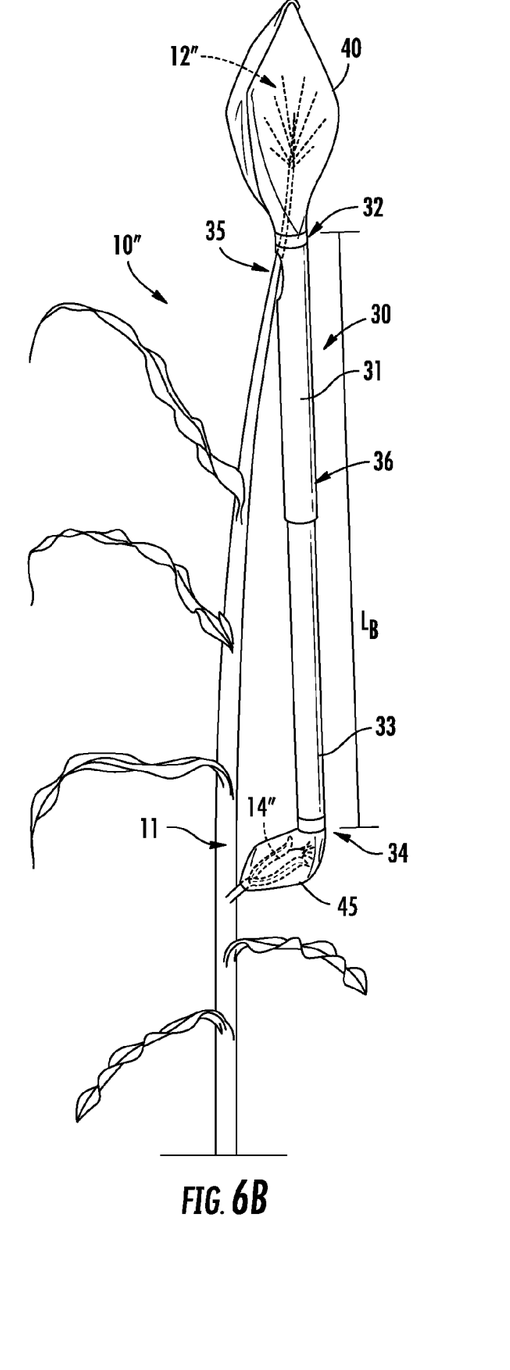
FIG. 6B illustrates a maize plant and a telescoping directed pollination apparatus configured for delivering grains of pollen in accordance with another example embodiment of the present invention.

As noted above, in some embodiments the directed pollination apparatus may be adjustable. FIGS. 6A and 6B illustrate a directed pollination apparatus 30 having a telescoping rigid tube 36 attached to two different maize plants 10',10", in which the distance between the respective tassels 12',12" and the ear shoots 14',14" are different. In the depicted embodiment, the directed pollination apparatus 30 includes a hollow rigid tube 36 having a first end 32, a second end 34, a channel defined therebetween, and an opening 35 located proximate the first end 32. A tassel bag 40 is attached to the first end 32 and a shoot bag 45 is attached to the second end 34. The rigid tube 36 of the depicted embodiment includes multiple sections 31, 32, one of which slides into another. In such a manner, the overall length of the telescoping directed pollination apparatus 30 may be adjustable. In the depicted embodiment, the distance between tassel 12' and ear shoot 14' in maize plant 10' is shorter than the distance between the tassel 12" and the ear shoot 14" in maize plant 10". Thus, for example, FIG. 6A illustrates the directed pollination apparatus 30 attached to a maize plant 10' wherein the length of the rigid tube 36 has been adjusted to a length $L_A$. A such, this allows the rigid tube 36 to be positioned so that it is in a relatively vertical position, thus providing an optimal path for the grains of pollen to reach the ear shoot 14'. FIG. 6B illustrates the directed pollination apparatus 30 attached to the other maize plant 10" wherein the length of the rigid tube 36 has been extended to a length $L_B$. As such, this allows the rigid tube 36 to be positioned so that it is also in a relatively vertical position, thus providing an optimal path for the grains of pollen to reach the ear shoot 14" for this maize plant 10" as well.

Figure 7:
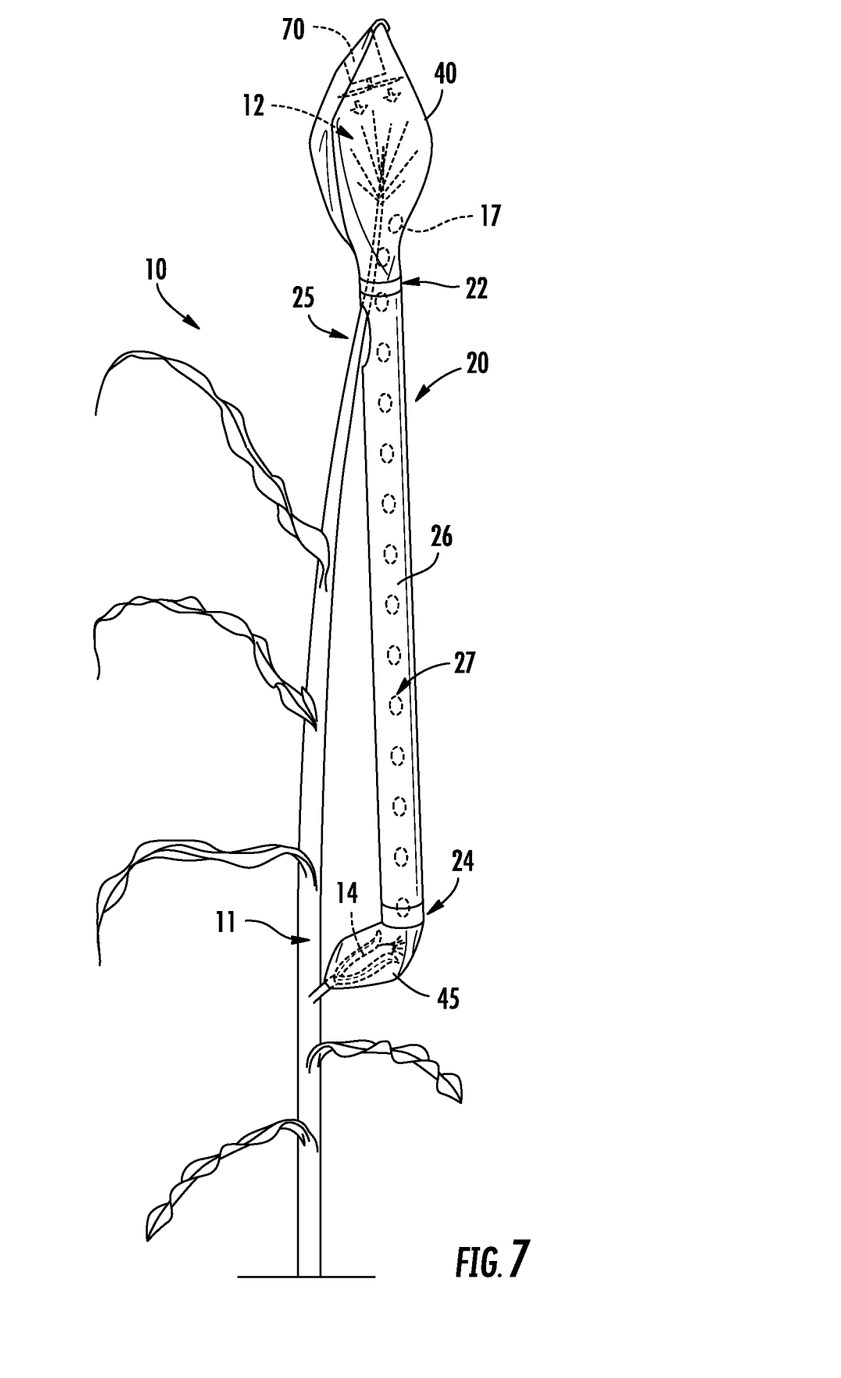
FIG. 7 illustrates a maize plant and a directed pollination apparatus configured for delivering grains of pollen in accordance with another example embodiment of the present invention.

FIG. 7 illustrates a directed pollination apparatus 20 attached to a maize plant 10 in accordance with another example embodiment of the present invention. In the depicted embodiment, the directed pollination apparatus 20 comprises a hollow rigid tube 26 having a first end 22 and a second end 24 and a channel defined therebetween. An opening 25 is disposed in the rigid tube 26 proximate the first end 22, which is configured to receive the tassel 12 of the maize plant 10. In the depicted embodiment, a tassel bag 40 is attached to the first end 22 of the rigid tube 26, and a shoot bag 45 is attached to the second end 24 of the rigid tube 26. The tassel bag 40 of the depicted embodiment is configured to receive the tassel 12 of the maize plant 10, and the shoot bag 45 is configured to receive the ear shoot 14 of the maize plant 10. In such a manner, the rigid tube 26 of the apparatus 20 defines a path 27 for the pollen grains 17 (shown in the drawing, for simplicity, as a series of circles) to transfer from the tassel 12 to the ear shoot 14 once the tassel 12 of the maize plant 10 begins to shed pollen. The depicted embodiment also includes a fan 70, which, in some embodiments, may further aid in the transfer of pollen from the tassel 12 to the ear shoot 14 along the path 27. Although in other embodiments, the fan could be placed anywhere about the directed pollination apparatus 20, in the depicted embodiment the fan 70 is positioned in the tassel bag 40, above the tassel 12, and generates a flow of air that travels past the tassel 12, along the path 27, toward the ear shoot 14. In the depicted embodiment, the fan 70 may be powered via battery power, however in other embodiments the fan could have a variety of power sources, including, but not limited to, solar power (such as, for example, via a solar panel attached to the outside of the directed pollination apparatus), or an alternating current power source. In other embodiments, other devices may be used to aid in transferring pollen from the tassel to the ear shoot. For example, in another embodiment a negative pressure device could be placed in the apparatus 20 proximate the ear shoot 14 in order to aid in drawing pollen grains along the path 27 from the tassel 12 to the ear shoot 14.

Methods for directed pollination of a maize plant will now be described. While the description may generally describe operations conducted by embodiments of the apparatuses 20, 30 illustrated in FIGS. 2-7, it should be noted that this is for purposes of brevity only. In this regard, various other ones of the above-described apparatuses may be employed to conduct the methods that will be described below.

Figure 8:
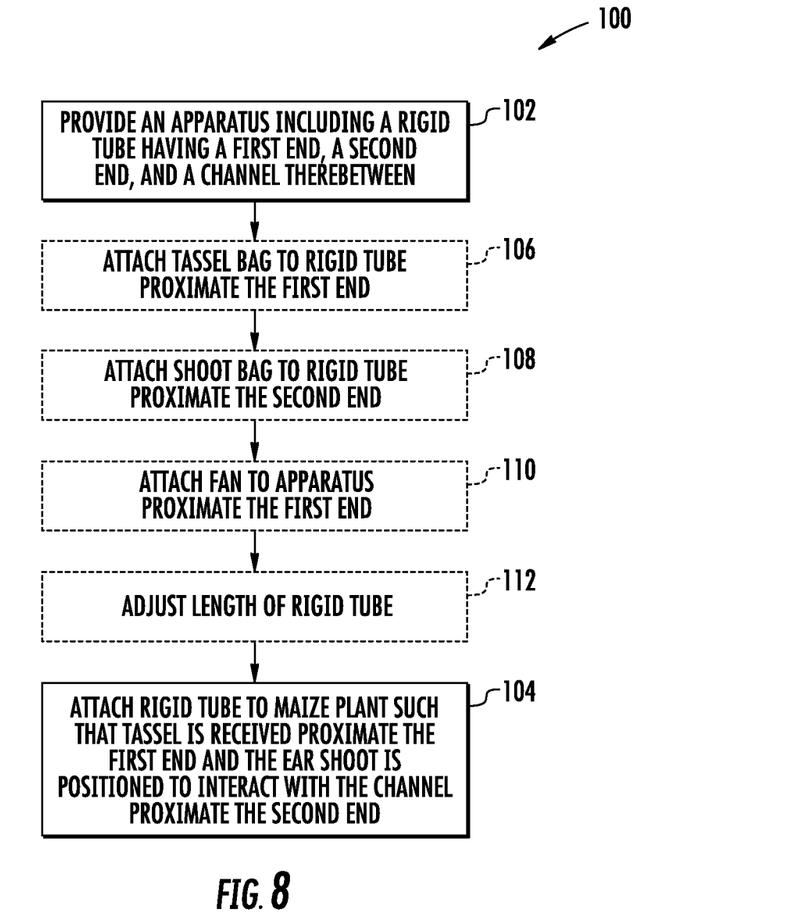
FIG. 8 illustrates a method for delivering grains of pollen in accordance with another example embodiment of the present invention.

FIG. 8 illustrates an example embodiment of a method for directed pollination of a maize plant. As illustrated, the method comprises providing an apparatus including a rigid tube having a first end, a second end, and a channel defined therebetween at step 102; and attaching the rigid tube to a maize plant such that the tassel of the maize plant is received proximate the first end of the rigid tube and the ear shoot of the maize plant is positioned to interact with the channel proximate the second end of the rigid tube at step 104. The method may also comprise attaching a tassel bag to the rigid tube proximate the first end at step 106. The method may also comprise attaching a shoot bag to the rigid tube proximate a second end at step 108. The method may also comprise attaching a fan to the apparatus proximate the first end at step 110. The method may also comprise adjusting a length of the rigid tube at step 112. It should be noted that although FIG. 8 shows steps 102-112 occurring in a particular order, the present invention contemplates one or more steps occurring in any order. In some embodiments, attaching the rigid tube to the maize plant occurs at any time before flower emergence to later in flower development.

Figure 9:
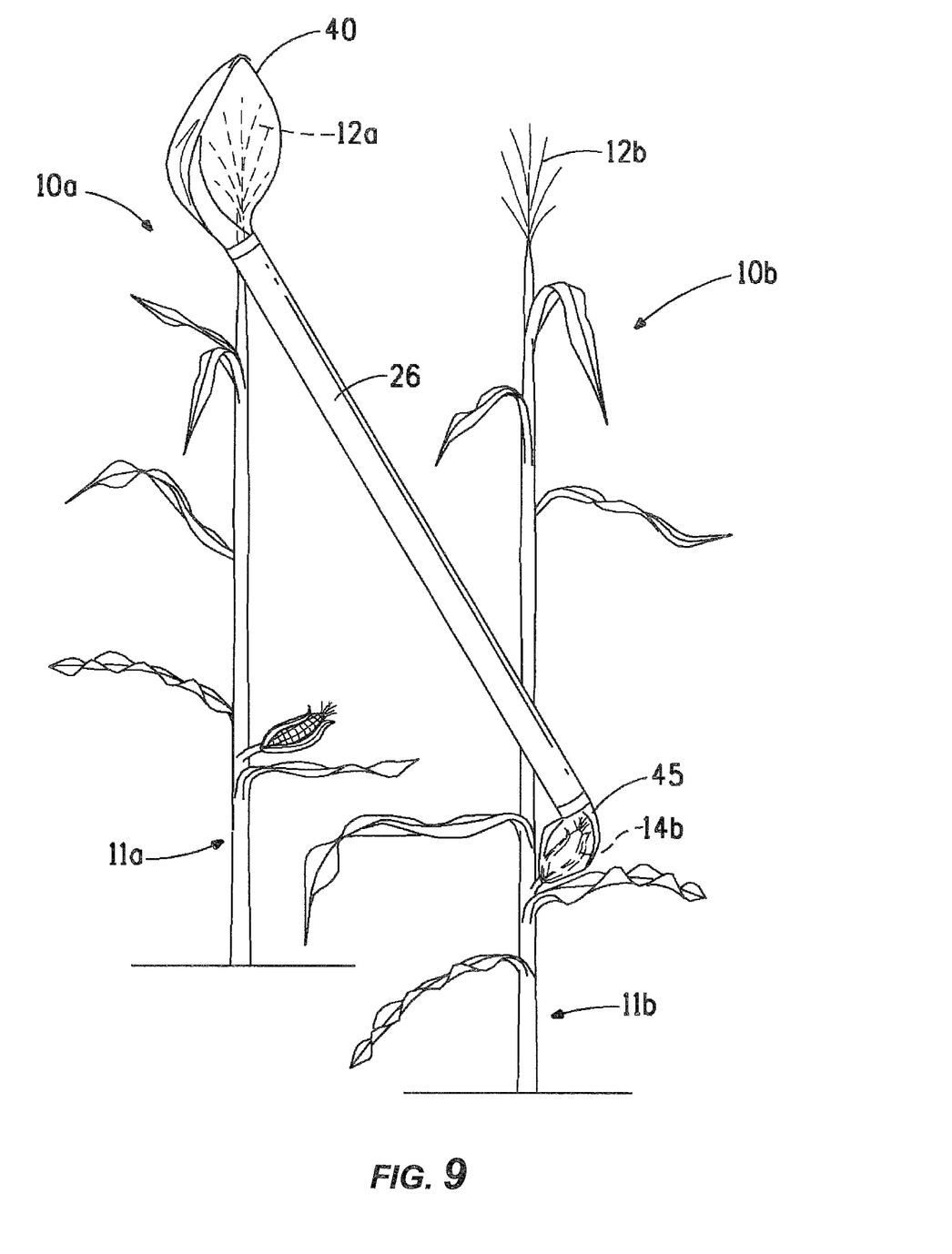
FIG. 9 illustrates directed cross-pollination between two different maize plants in accordance with another example embodiment of the present invention.

In various embodiments, the apparatuses and methods of the preset invention may also be used for directed cross-pollination between plants of the same species and/or for hybridization across different species. For example, FIG. 9 illustrates directed cross-pollination between two different maize plants 10a and 10b in accordance with another example embodiment of the present invention. As shown in the figure, a top portion of a first maize plant 10a is inserted into an opening of the rigid tube 26 such that the tassel 12a of the first maize plant 10a is received by a rigid tube 26 and extends into a tassel bag 40. The ear shoot 14b of a second maize plant 10b is received into a shoot bag 45, which is connected to the other end of the tube 26. Applicant notes that FIG. 9 is merely an example, and thus the various apparatuses and methods described herein may be applicable to cross-pollination between various plants of the same species.

Figure 10:
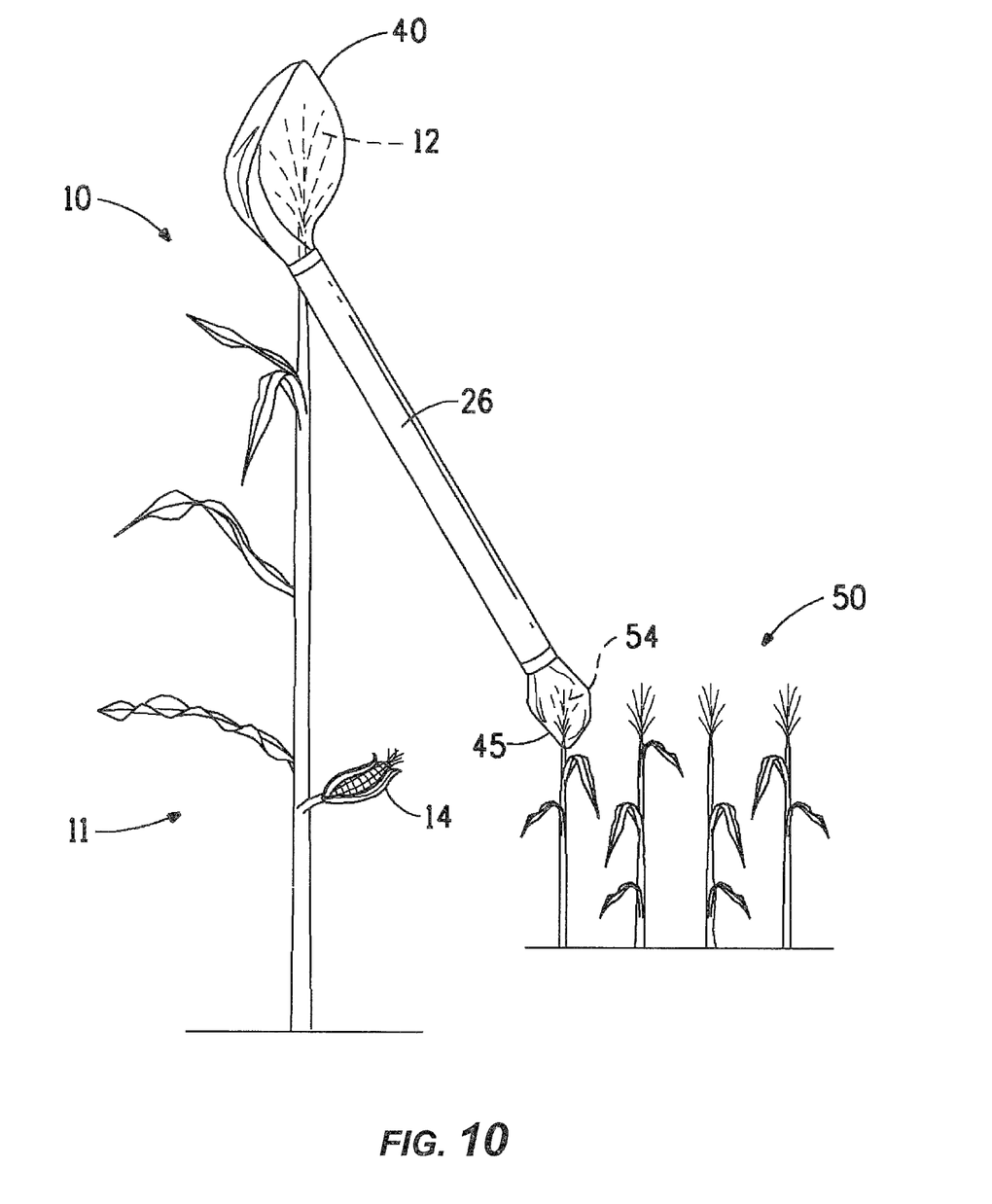
FIG. 10 illustrates directed cross-pollination between species in accordance with another example embodiment of the present invention.

FIG. 10 illustrates cross-pollination across different species in accordance with another embodiment of the present invention. In particular, a top portion of a first maize plant 10 is inserted into an opening of the rigid tube 26 and the tassel 12 of the first maize plant 10 is received by the rigid tube 26 and extends into a tassel bag 40. The pollen receiving portion 54 of a plant 50 of another species is then received by a shoot bag 45, which is connected to the other end of the tube 26. Applicant notes that FIG. 10 is merely an example, and thus the various apparatuses and methods described herein may be applicable to cross-pollination between various plants of different species.

By employing the methods and/or the apparatuses disclosed herein, directed pollination of a plant, such as, for example, a maize plant, may be facilitated while minimizing the possibility of unintended cross-contamination. Many modifications and other embodiments of the invention set forth herein will come to mind to one skilled in the art to which these invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for directed pollination of a maize plant, wherein the maize plant defines a tassel and an ear shoot, the apparatus comprising:
    a rigid tube having a first end, a second end, and a channel defined therebetween, and a fan such that the fan is fluidly connected to the channel, wherein the fan is configured to create air flow to transfer pollen through the channel to the second end;
    wherein the rigid tube is a telescoping rigid tube such that the overall length of the rigid tube is adjustable,
    wherein the rigid tube is configured to receive a tassel of a maize plant proximate the first end,
    wherein the rigid tube is configured to interact with a ear shoot of a maize plant proximate the second end, and
    wherein the channel defines a path between the first end and the second end so as to enable transfer of pollen from the first end to the second end.

2. The apparatus of claim 1, wherein the second end defines a second end opening that is configured to receive an ear shoot of a maize plant.

3. The apparatus of claim 1, wherein the second end is configured to interact with a shoot bag such that pollen may transfer from a tassel to an ear shoot of the maize plant through the channel and the shoot bag.

4. The apparatus of claim 1, wherein the first end is configured to interact with a tassel bag such that a tassel is received into the tassel bag.

5. The apparatus of claim 1, wherein the rigid tube defines an opening proximate the first end, and wherein the opening is configured to receive a tassel therethrough.

6. The apparatus of claim 1, wherein rigid tube is made from at least one of the following materials: PVC plastic, polycarbonate, polypropylene, plastic, cardboard, or a compostable material.

7. The apparatus of claim 1, wherein the path is enclosed so as to prevent unintended cross-pollination.

8. The apparatus of claim 1, wherein the channel is defined by a smooth surface to prevent obstruction of pollen transferring from a tassel to an ear shoot.

9. An apparatus for directed cross-pollination of a maize plant, comprising:
    a rigid tube having a first end, a second end, a channel defined therebetween, and a fan such that the fan is fluidly connected to the channel, wherein the fan is configured to create air flow to transfer pollen through the channel to the second end;
    wherein the rigid tube is configured to receive a tassel of a first maize plant proximate the first end,
    wherein the rigid tube is configured to interact with an ear shoot of a second maize plant proximate the second end, and
    wherein the channel defines a path between a tassel of a first maize plant and an ear shoot of a second maize plant so as to enable transfer of pollen from a tassel of a first maize plant to an ear shoot of a second maize plant.

10. An apparatus for directed cross-pollination of a plant, comprising:
    a rigid tube having a first end, a second end, a channel defined therebetween, and a fan such that the fan is fluidly connected to the channel, wherein the fan is configured to create air flow to transfer pollen through the channel to the second end;
    wherein the rigid tube is configured to receive a pollen source portion of a plant of a first species proximate the first end,
    wherein the rigid tube is configured to interact with a pollen receiving portion of a plant of a second species proximate the second end, and
    wherein the channel defines a path between a pollen source portion of a plant of a first species and a pollen receiving portion of a plant of a second species so as to enable transfer of pollen from a pollen source portion of a plant of a first species to a pollen receiving portion of a plant of a second species.

\* \* \* \* \*